United States Patent [19]
Graether

[11] Patent Number: 5,632,284
[45] Date of Patent: May 27, 1997

[54] BARRIER EYE DRAPE AND METHOD OF USING SAME

[76] Inventor: John M. Graether, 611 Elmwood Dr., Marshalltown, Iowa 50158

[21] Appl. No.: 651,325

[22] Filed: May 22, 1996

[51] Int. Cl.$^6$ .................................................. A61B 19/00
[52] U.S. Cl. .......................................... 128/849; 128/853
[58] Field of Search ..................................... 128/849–856; 604/35, 902

[56] References Cited

U.S. PATENT DOCUMENTS

| | | |
|---|---|---|
| 3,397,692 | 8/1968 | Creager, Jr. et al. . |
| 3,650,267 | 3/1972 | Anderson . |
| 3,721,234 | 3/1973 | Hadtke ............................... 128/853 |
| 3,763,857 | 10/1973 | Schrading ........................... 128/853 |
| 3,863,639 | 2/1975 | Kleaveland . |
| 4,705,500 | 11/1987 | Reimels ................................. 604/35 |
| 4,966,168 | 10/1990 | Glassman . |
| 5,127,423 | 7/1992 | Draeger . |
| 5,213,114 | 5/1993 | Bailey, Jr. . |
| 5,345,946 | 9/1994 | Butterworth et al. . |
| 5,464,025 | 11/1995 | Charles ................................ 128/849 |

*Primary Examiner*—Michael A. Brown
*Attorney, Agent, or Firm*—Zarley, McKee, Thomte, Voorhees & Sease

[57] ABSTRACT

A surgical drape includes inner and outer flexible tubular members having a flexible drape of sheet material extending between them and a pumping device for pumping fluid into the inner and outer members. Also disclosed is a tool for depositing the surgical drape around the eye of a patient. A method of using the surgical drape as a barrier eye drape includes the steps of inserting the inner tube underneath the eyelids and around the eyeball of the patient, pumping fluid into the inner tube so as to inflate it into engagement with the eyelids and create retaining pressure, depositing the outer tube on the outer surface of the eyelids, pumping fluid into the outer tube so as to inflate it and draw the drape material into substantial planar contact with the interior and anterior portions of the eyelids, thereby retracting the eyelids outwardly and enlarging an opening between them to allow access to the eye for surgical procedures and provide a waterproof seal.

12 Claims, 7 Drawing Sheets

BARRIER EYE DRAPE AND METHOD OF USING SAME

BACKGROUND OF THE INVENTION

The present invention relates to surgery and the medical field. In particular, this invention relates to ophthalmology and, more particularly, to an eye drape for covering body surfaces surrounding the eyeball and for protecting the eyeball during eye examination and surgery.

It is well known that drapes can be useful during examination or surgery on various parts of the body. The drapes give the health care provider access for examination. In the case of surgery, the drapes give the surgeon access to the surgical field while generally isolating that part of the body from other body parts. Thus, drapes usually help reduce the chances of infection occurring after examination or surgery.

Due in part to the small size and intricate structure of the human eye, draping it is particularly difficult. Laying a drape sheet over the eye and providing an access opening therein still leaves the eyelids in the surgical field. Generally it is desirable to retract the eyelids to provide the surgeon greater access to the eyeball. It is also desirable to remove the eyelids and eyelashes from the surgical field.

The ophthalmologic drape disclosed in U.S. Pat. No. 5,213,114, which issued May 25, 1993 to Bailey, attempts to isolate the eyelids from the eyeball and the surgical field. However, that drape lacks means for effectively sealing off the eyelids from the eyeball. Furthermore, the drape disclosed in the Bailey patent is difficult to install and keep in place.

The present devices and methods for draping the eye during ophthalmic surgery are cumbersome, do not consistently isolate the surgical field from the lids and lashes, and may interfere with surgical equipment or maneuvers. Existing drapes fail to isolate the surgical field by providing a waterproof barrier between the conjunctival surface of the eye and the lids. Additional retractors of the lids such as a speculum are typically required. Existing drapes fail to provide a suitably large palpebral aperture for surgical maneuvers.

There is a need for an eye drape which is easy to install and yet will remain securely in place during the examination and/or surgery.

Therefore an object of the present invention is the provision of barrier eye drape for covering the anterior and interior surfaces of the eyelids to protect the eyeball during examination and surgery.

A further object of this invention is the provision of an improved method of draping a patient's eye or surgical area.

A further object of this invention is the provision of a barrier eye drape which will consistently isolate the surgical field from the eyelids, eyelashes, or other body parts adjacent the surgical area, without interfering with surgical equipment or maneuvers.

A further object of this invention is the provision of an inflatable, waterproof barrier drape insertable between the conjunctival surface of the eye and the eyelids.

A further object of this invention is the provision of an eye drape which provides a large palpebral aperture for surgical maneuvers and eliminates the need for additional retractors.

A further object of this invention is the provision of an eye drape that is quick and simple to install.

A further object of this invention is the provision of an eye drape that can be disposable.

A further object of this invention is the provision of an eye drape that is comfortable for the patient, even under topical anesthesia.

A further object of this invention is the provision of an eye drape which is inexpensive and simple to manufacture.

A further object of this invention is the provision of a surgical drape having a pair of concentric inflatable tubes interconnected with a flexible membrane.

These and other objects of the present invention will be understood from the drawings, description and claims which follow.

SUMMARY OF THE INVENTION

The present invention relates to a surgical drape for isolatating an incision or particular body part. The present invention is particularly well adapted to be used as a barrier eye drape during ophthalmic surgery or examination. The surgical drape includes an inner tube, a larger diameter outer tube, a flexible drape of sheet material extending between the inner and outer tubes, and means for pumping fluid into the inner and outer tubes so as to draw the drape into substantial planar contact with the interior and anterior portions of the incision or body part.

As a barrier eye drape, the surgical drape of this invention has an inner tube adapted for inserting underneath the eyelids and extending around the eyeball. When the inner tube is placed against the eyeball and inflated, it becomes securely retained in the cul-de-sac of the eye. Then when the outer tube is inflated, the drape of sheet material attached thereto is drawn into substantial planar contact with the interior and anterior portions of the eyelids. Thus, the barrier eye drape provides retraction of the eyelids and establishes a large aperture around the eyeball for surgery or examination.

A tool for holding the barrier eye drape and inserting it into the eye is also provided. With or without such a tool, the basic method of inserting the barrier eye drape is quick, simple, and easy to execute. First, the surgeon inserts the inner tube underneath the eyelids and extends it around the eyeball. Fluid is then pumped into the inner tube, inflating it into engagement with the eyelids and retaining it there. The surgeon then deposits the outer tube on the outer surface of the eyelids before pumping fluid into it. Inflation of the outer tube draws the drape material into substantial planar contact with the interior and anterior portions of the eyelids, thereby retracting them outwardly and enlarging an opening between them. Thus, the barrier eye drape provides access to the eye for surgical procedures and creates a waterproof seal between the surgical field and the surrounding area of the body.

DETAILED DESCRIPTION OF THE PREFERRED EMBODIMENT

Figures 1, 1A, 1B:
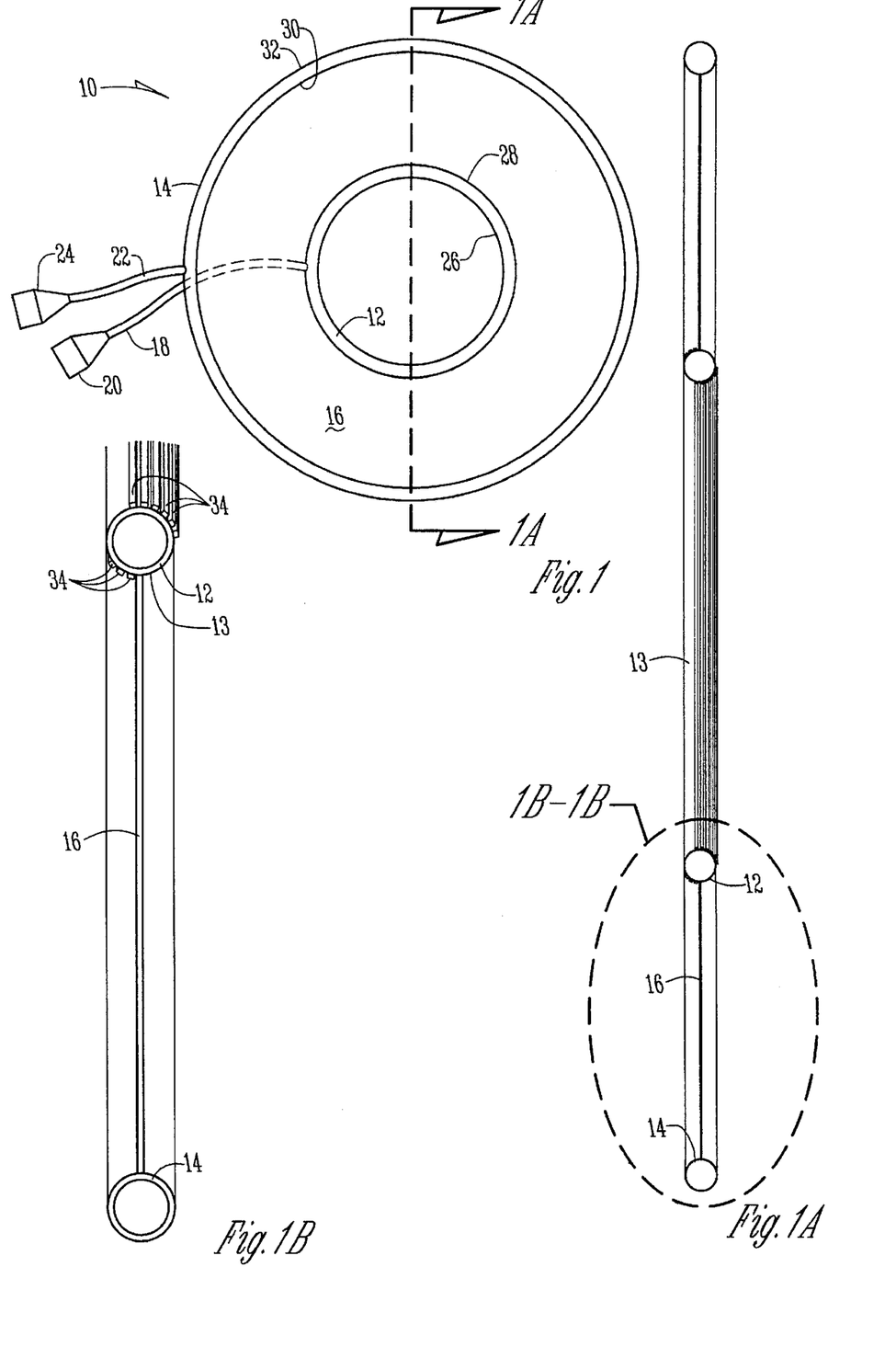
FIG. 1 is a top plan view of the eye drape of the present invention.
FIG. 1A is an enlarged cross sectional view of the eye drape of this invention taken along line 1A—1A in FIG. 1.
FIG. 1B is an enlarged view of the area designated 1B—1B in FIG. 1A.

In the drawings and the description which follows, the barrier eye drape of the present invention is generally denoted by the reference numeral 10. As shown in FIG. 1, the eye drape 10 includes an inner, hollow tubular member 12 and an outer, hollow tubular member 14 interconnected by a thin, elastic membrane-like member 16. The inner and outer tubular members 12, 14 and the interconnecting web 16 are constructed of a flexible latex material which is not only elastic but allows the eye drape to be sterilized or come pre-sterilized.

A filling tube 18 has one end fluidly connected to the inner tubular member 12 and another end which terminates in a self-sealing plug 20. Similarly, a filling tube 22 has one end fluidly connected to the outer tubular member 14 and another end which terminates in a self-sealing plug 24. The self-sealing plugs 20, 24 are well known in the medical field.

When filled with a suitable non-toxic fluid including but not limited to a gas (such as air) or a liquid (such as water or a sterile balanced salt solution), the inner and outer members 12, 14 inflate into concentric rings as shown in FIGS. 1, 1A and 1B. The inner tubular member 12 includes an inner diameter 26 which defines an aperture through the drape 10. The inner member 12 may have a tapered, flattened shape or a thicker wall at its inner diameter 26 to provide rigidity prior to inflation. In elastic fibers within the inner tube 12 could be used to limit its expansion during inflation. The inner tubular member 12 also includes an outer diameter 28. Of course, it is contemplated that other shapes may be used without detracting from the invention. For instance, an elliptical shape may also provide a good fit on the patient's eye. Likewise, the outer tubular member 14 includes an inner diameter 30 and an outer diameter 32.

As seen in FIGS. 1A and 1B, striations in the form of ribs, ridges or other surface irregularities are provided on the outer surface 13 of the inner tubular member 12. Preferably the striations 34 comprise a plurality of ridges extending circumferentially around the outer diameter 28 of the toroidal inner member 12. The striations 34 help grip the tissue around the eye.

Figure 2:
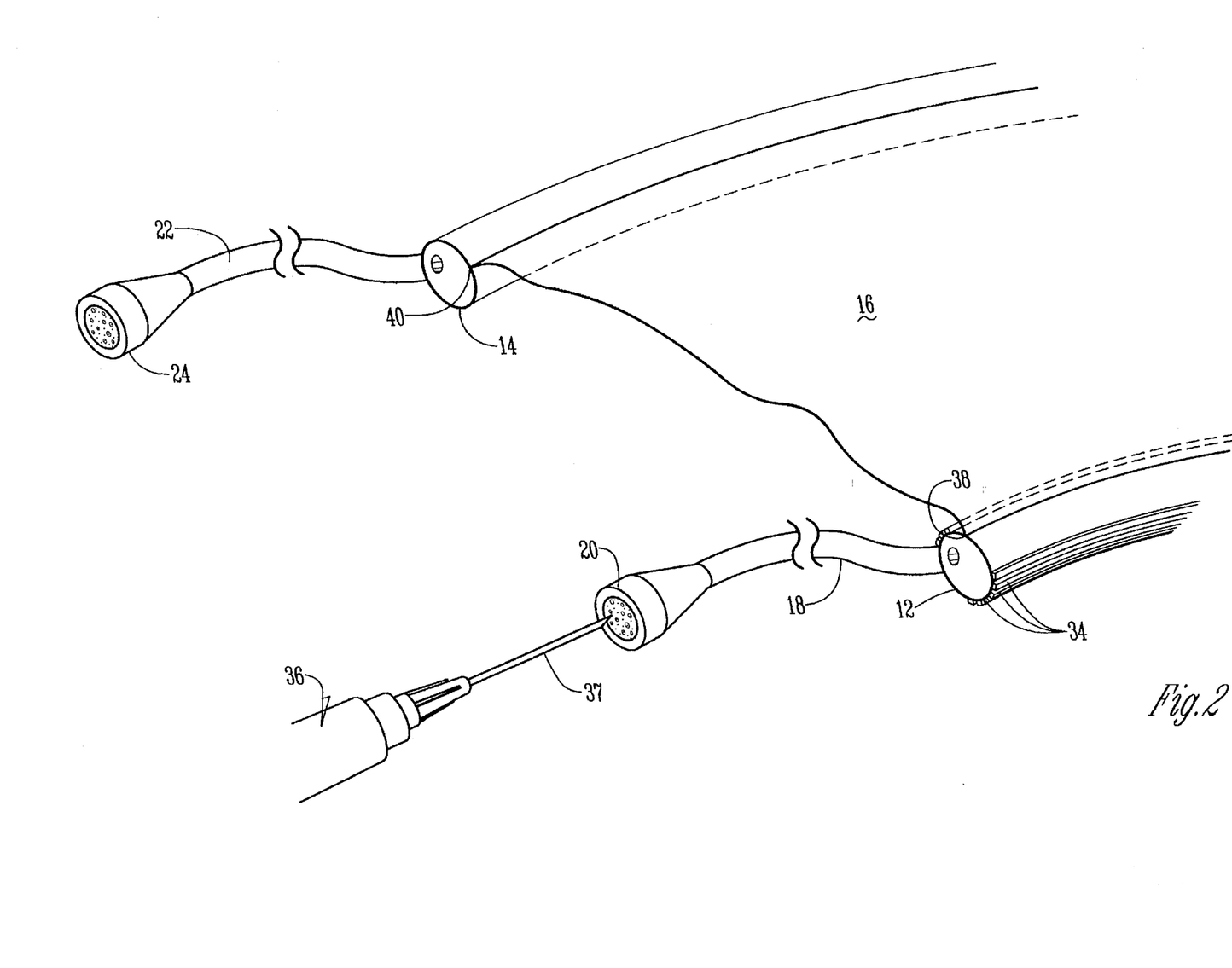
FIG. 2 is an enlarged partial perspective view of the eye drape of this invention which shows a means for inflating the tubular members.

Referring to FIG. 2, a conventional syringe 36 having a needle 37 is provided for inflating the tubular members 12, 14 with fluid through the self-sealing plugs 20, 24 on the filling tubes 18, 22. Alternatively, one can use a small conventional air pump with a bulb squeezable by hand to inflate the tubes 12, 14.

The drape membrane 16 joins the inner and outer tubular members 12, 14 along airtight and waterproof seams 38, 40 respectively. The drape membrane 16 itself comprises a thin sheet of airtight, waterproof material. Thus, the drape member 16 and the inner and outer tubular members 12, 14 together form an airtight and waterproof barrier for isolating a surgical field around the eyeball.

In use, the eye drape 10 of the present invention is inserted into the patient's eye as shown in FIGS. 3-5A. The relevant features of the patient's eye 42 appear in FIG. 3. The eyeball 44 includes upper and lower eyelids 46, 48 respectively therearound. Both of the upper and lower eyelids 46, 48 include conjunctival tissue which forms a cul-de-sac 50. Upper eyelashes 52 extend from the upper eyelid 46 and lower eyelashes 54 extend from the lower eyelid 48.

Figures 3, 3A, 4, 4A:
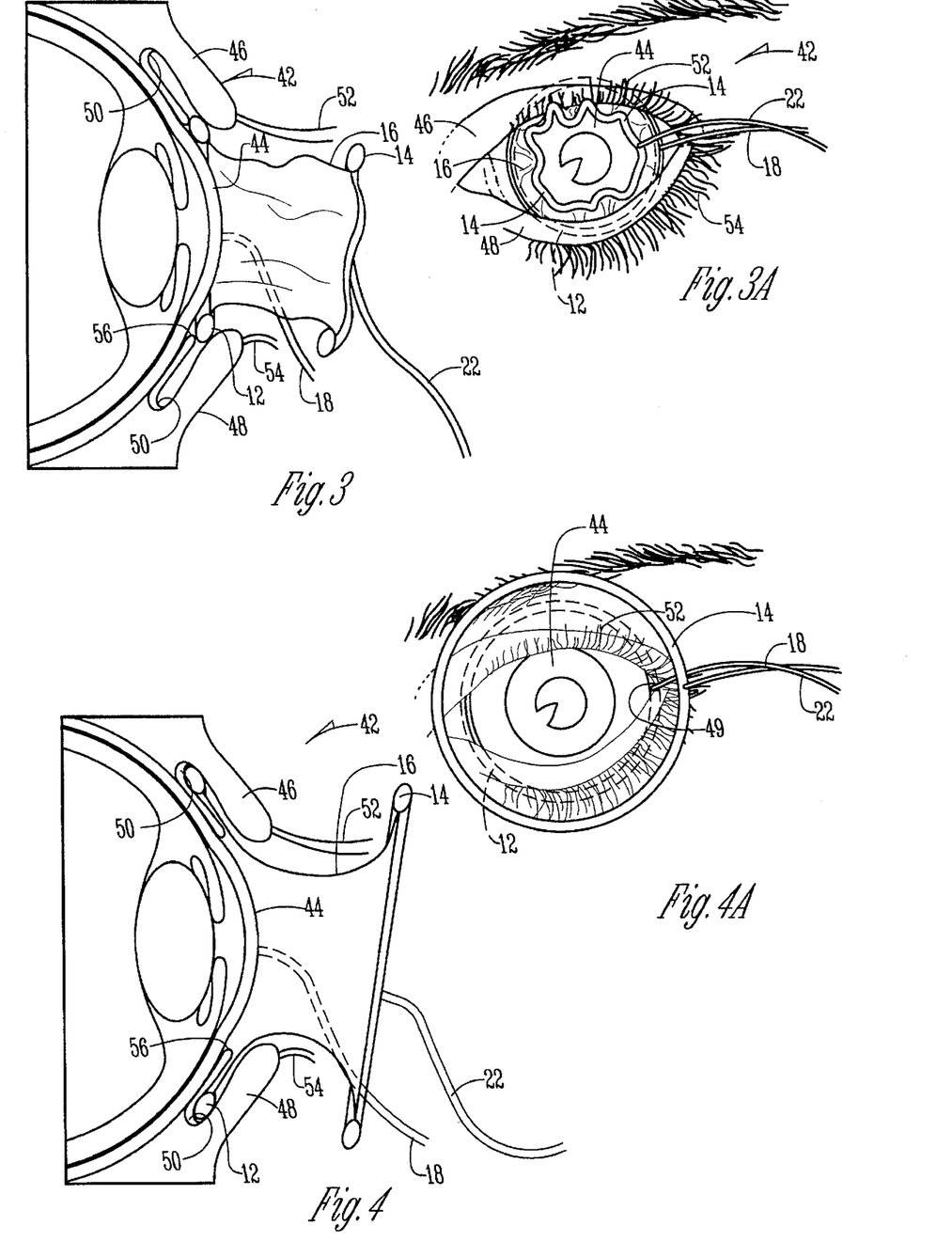
FIG. 3 is an enlarged cross-sectional view of the eye drape of this invention as initially inserted into the patient's eye. Cross-hatching has been omitted to improve readability.
FIG. 3A is an enlarged frontal view of the eye and eye drape shown in FIG. 3.
FIG. 4 is an enlarged cross-sectional view of the eye and eye drape of this invention following the inflation of the inner tubular member. Cross-hatching has been omitted to improve readability.
FIG. 4A is an enlarged frontal view of the eye and eye drape shown in FIG. 4.

After the application of a topical anesthesia to the conjunctiva, the inner tubular member 12 can be compressed, and inserted between the eyelids 46, 48 and the anterior portion of the eyeball 44. In the uninflated state, the tubular member 12 is very flexible and easily compressed thereby allowing it to pass between the eyelids 46, 48 so that it comes to lie on surface of the globe or eyeball 44 concentric with the limbus 56. The drape membrane 16 and the uninflated outer tubular member 14 extend forwardly from the inner tubular member 12. Care should be taken to ensure that the fill tubes 18, 22 extend away from the inner and outer tubular members 12, 14 and the eyeball 44, as shown in FIGS. 4 and 4A. The fill tube 18 will naturally tend to exit at the outer can thus 49.

The inner tubular member 12 is inflated with fluid so that it expands into the cul-de-sac 50. In its inflated or expanded state, the inner member 12, with the aid of the striations 34, firmly engages the walls of the cul-de-sac 50. Thus, both pressure from the overlying portion of the eyelids 46, 48 and the internal fluid pressure within the tubular member 12 prevent movement of the drape 10 relative to the cul-de-sac 50. The inner tubular member 12 effectively seals off the eyelids 46, 48 from the eyeball 44 with an airtight, waterproof barrier. It is also contemplated that the inner tubular member 12 could fill the cul-de-sac 50 so completely that it limits voluntary movement of the globe or eyeball by creating uniform traction on the bulbar conjunctiva.

Figures 5, 5A:
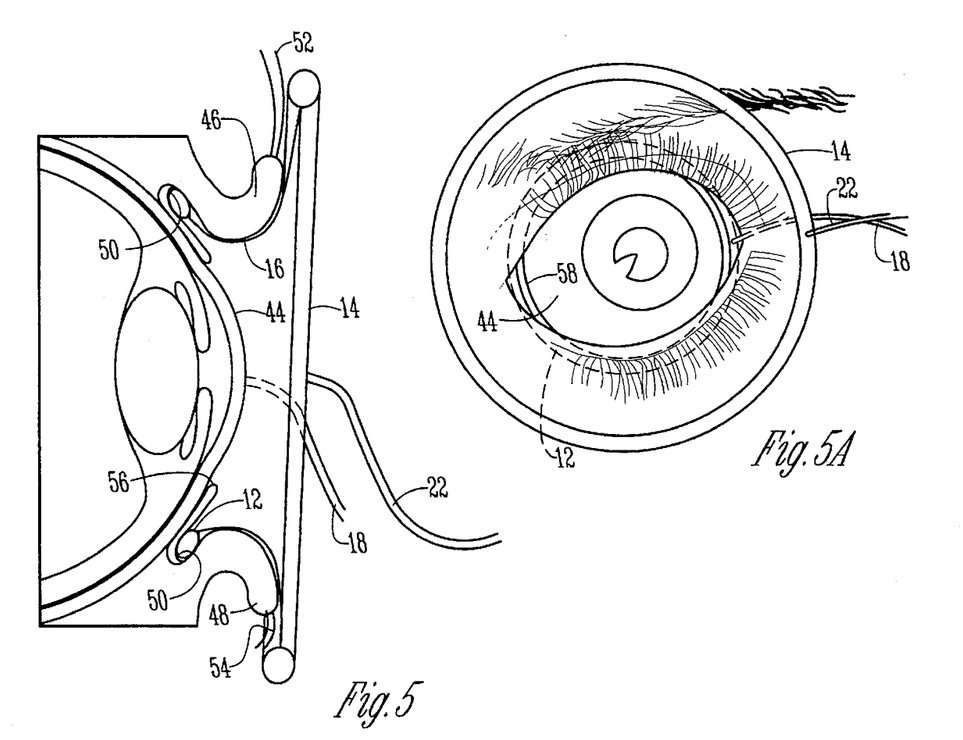
FIG. 5 is an enlarged cross-sectional view of the eye drape of the present invention installed in the patient's eye and shows both the inner and outer tubular members inflated. Cross-hatching has been omitted to improve readability.
FIG. 5A is an enlarged frontal view of the eye and eye drape shown in FIG. 5.

Referring to FIG. 5, the next step is to inflate the outer tubular member 14 through the fill tube 22. As the outer tubular member 14 expands, the drape membrane 16 moves with it, thereby pulling or drawing back the eyelids 46, 48. Meanwhile, the inner tubular member 12 remains fixed in the cul-de-sac 50. As best seen in FIG. 5A, a large palpebral aperture 58 is provided for surgery or examination. One skilled in the art will appreciate that the eyelids 46, 48 and the eyelashes 52, 54 are effectively isolated from the surgical field by the drape 10. Furthermore, the eye drape 10 of this invention is self-retaining and even provides adjustable retraction.

Figure 6:
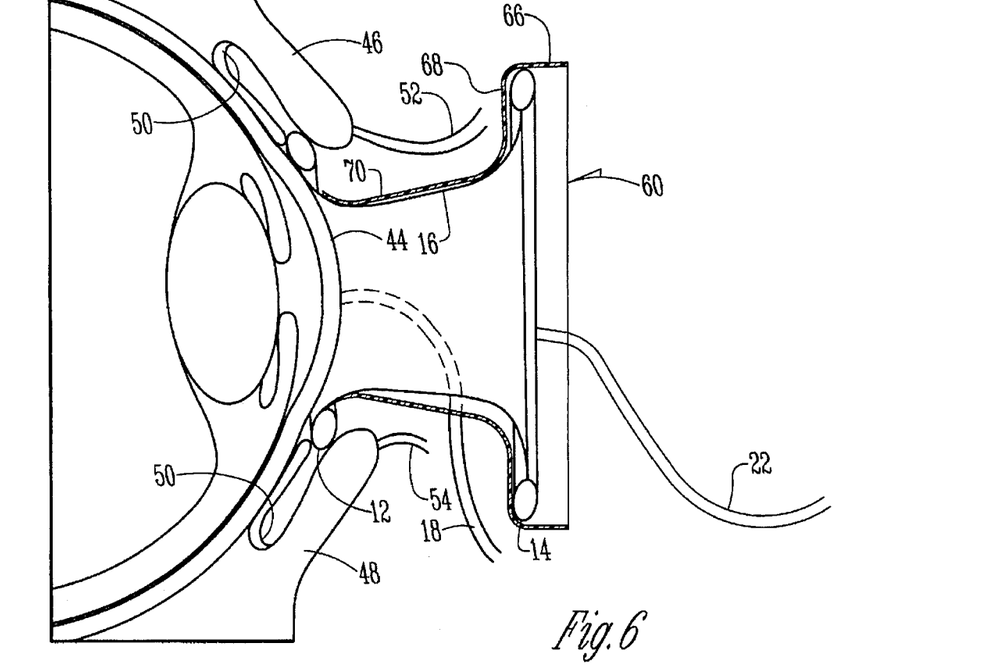
FIG. 6 is an enlarged cross-sectional view of the eye area which depicts a tool and method for installing the eye drape of the present invention into the eye. Some cross-hatching has been omitted to improve readability.
Figure 9:
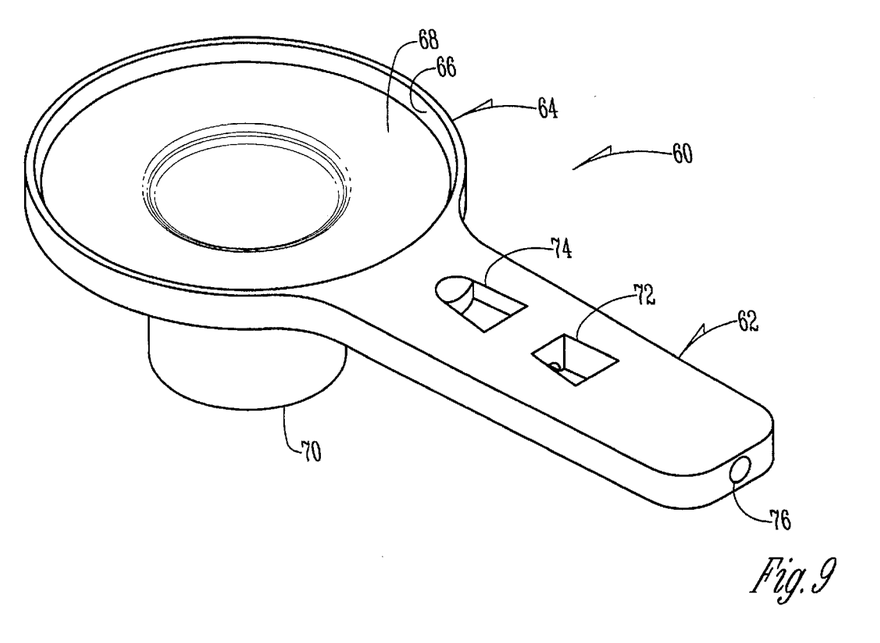
FIG. 9 is a perspective view of an insertion tool for installing the eye drape according to the present invention.

The present invention also includes a tool 60 for inserting the eye drape 10 into the eye of the patient. As best seen in FIG. 9, the tool 60 includes a handle portion 62 attached to a tubular portion 64. The tubular portion 64 includes a generally circular rim 66 which extends upwardly from a horizontal annular ledge 68. A hollow, cylindrical or conical tube 70 extends downwardly from the ledge 68. As best seen in FIG. 6, the hollow tube 70 receives the drape membrane 16, while the ledge 68 and rim 66 receive the outer tubular member 14. The length of the tube 70 is sized so as to allow the inner tubular member 12 to hang just below it.

Referring again to FIG. 9, receptacles 72, 74 receive the plugs 20, 24 of the fill tubes 18, 22. An access hole 76 extends through the handle portion 62 and intersects the receptacle 72 so as to allow insertion of the needle 37 into the plug 20. Receptacle 74 is merely a blind hole for storing the plug 24.

Figure 6A:
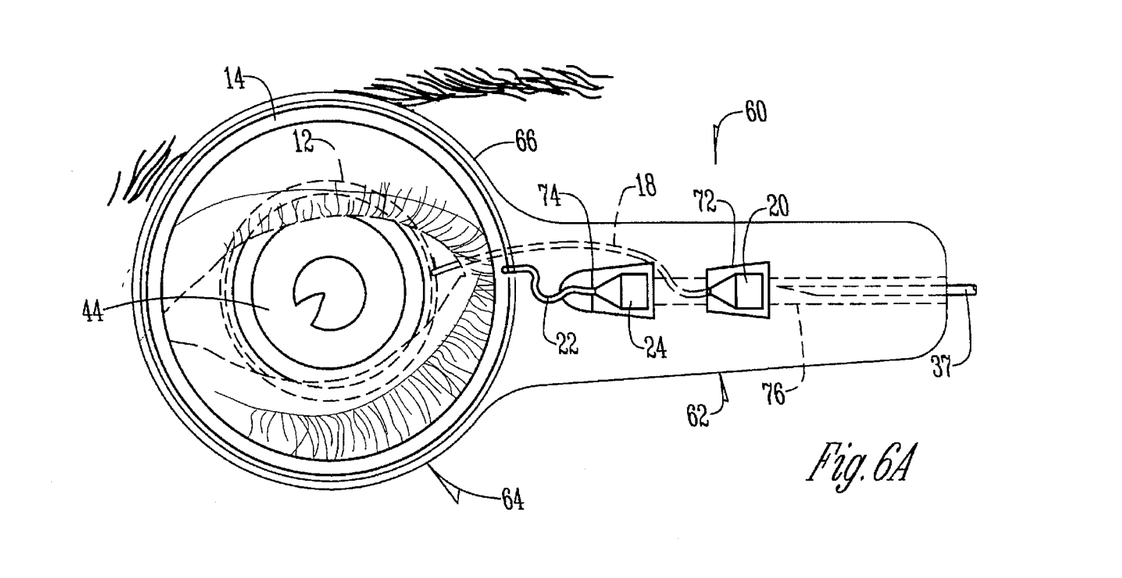
FIG. 6A is an enlarged frontal view corresponding to FIG. 6.

FIGS. 6–8A illustrate the method of using the insertion tool 60. The same basic steps described earlier with respect to installing the drape are followed with the aid of the tool 60. First, as seen in FIG. 6 and 6A, the inflatable eye drape 10 of the present invention can be attached to the insertion tool in a separate operation or can be delivered pre-packaged in its assembled state. The outer tubular member 14 rests on the ledge 68 adjacent the rim 66, the membrane 16 extends into the tube 70 of the tool 60, while the inner tubular member 12 is held to the bottom and outside surfaces of the dispensing portion 70.

It is contemplated that the bottom of the dispensing portion 70 of the tool 60 can be flared outwardly (see FIG. 6) for better placement of the inner tube 12 against the eyeball 44. It is also contemplated that a plurality of radially extending slots (not shown) can be formed through the dispensing portion 70 of the tool 60 adjacent its bottom. The flaccid inner tube 12 could be folder inwardly into these slots from the outside to take up any slack. The tube 12 would naturally exit the slots as the tube 12 was inflated.

The eyelids 46, 48 are spread manually and the dispensing portion 70 of the insertion tool 60 is applied to the surface of the eyeball 44 surrounding the cornea. This brings the inner tubular member 12 into contact with the eyeball 44 just beneath the plane of the eyelids 46, 48 and adjacent to the cul-de-sac 50. Then the needle 37 is inserted into the plug 20 through the access hole 76, as shown in FIG. 6A.

Figure 7:
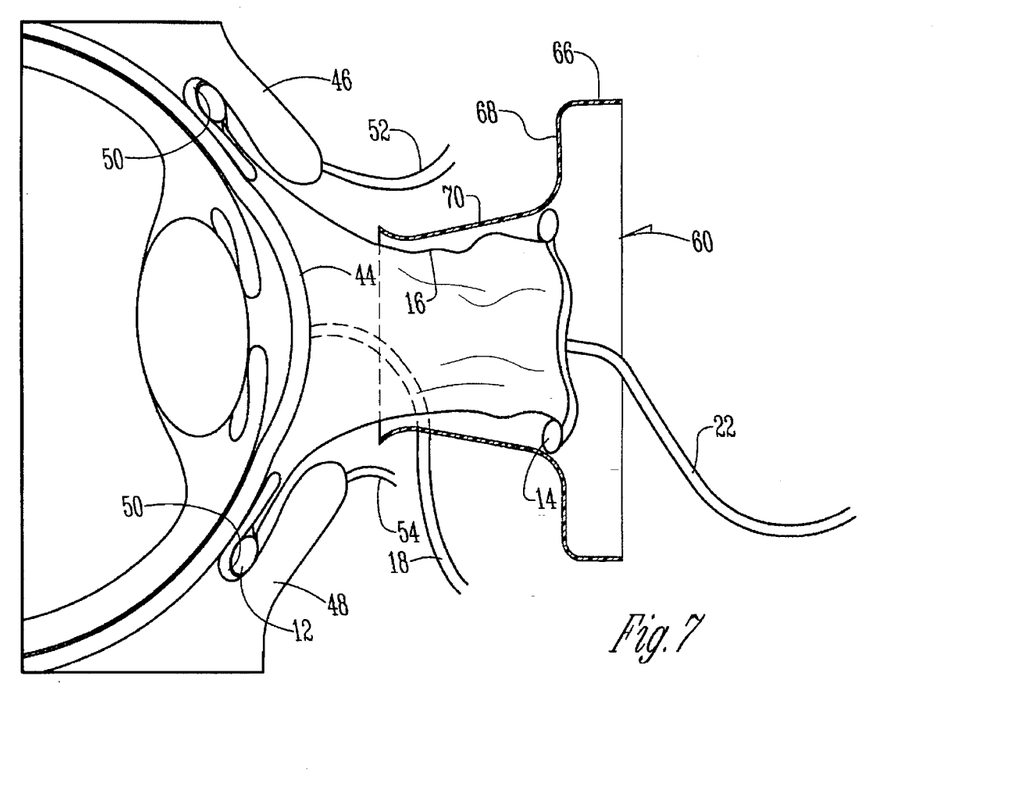
FIG. 7 is an enlarged cross-sectional view of the eye area which depicts the inflation of the inner tubular member and the initial removal of the insertion tool. Some cross-hatching has been omitted to improve readability.
Figure 7A:
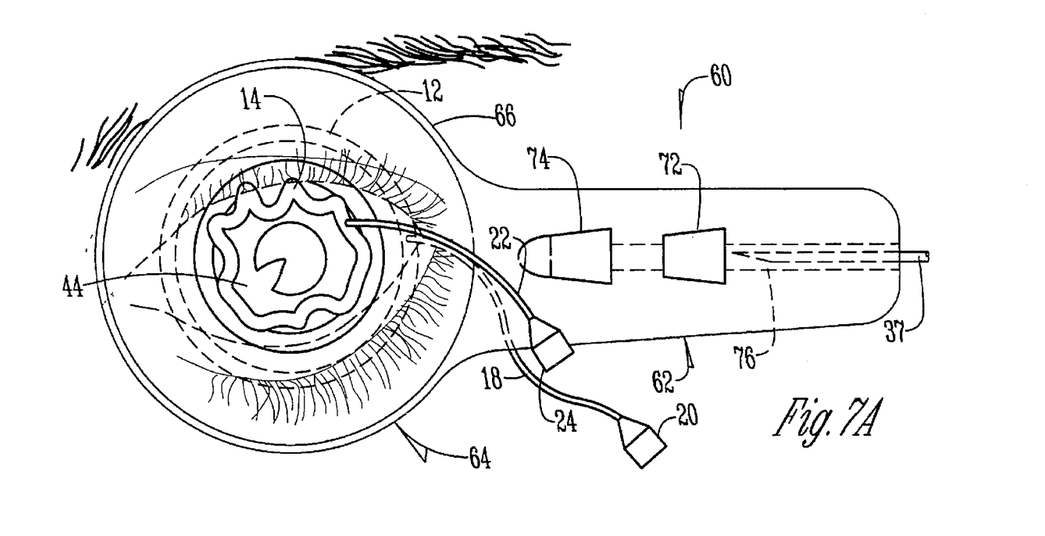
FIG. 7A is an enlarged frontal view corresponding to FIG. 7.

Referring to FIG. 7, the pumping means 36 fills or inflates the inner tube 12 with fluid, which causes the tube 12 to expand outwardly into the cul-de-sac 50. When the inner tube 12 is securely retained in the cul-de-sac 50, the syringe 36 can be withdrawn from the self-sealing plug 20. Then one removes the plug 20 from the receptacle 72 of the tool 60 (see FIG. 7A).

Next, the tool 60 is slowly pulled away from the eyeball 44, as shown in FIG. 7. The flaccid outer tube 14 is drawn into the tube 70 of the tool 60. The surgeon continues to pull the tool 60 away from the eyeball 44 until the outer tube 14 clears the bottom of the dispensing portion 70. The plug 24 is removed from the receptacle 24 whenever it is most convenient for the surgeon and least likely to fall into the patient's eye.

Figure 8:
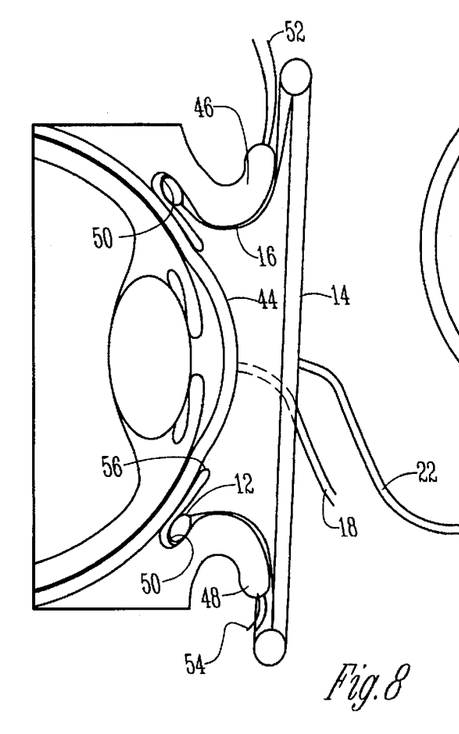
FIG. 8 is an enlarged cross-sectional view illustrating the installed position of the eye drape (following the inflation of the outer tubular member). Cross-hatching has been omitted to improve readability.
Figure 8A:
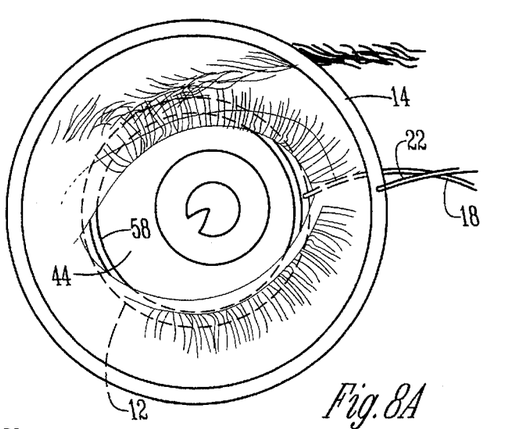
FIG. 8A is an enlarged frontal view corresponding to FIG. 8.

Then, as shown in FIG. 8, the surgeon uses the pumping means 36 to fill or inflate the outer tube 14. As the outer tube 14 expands, it retracts or draws back the eyelids 46, 48 due to the tension induced on the drape membrane 16 which extends between the inner and outer tubes 12, 14. Thus, an adjustably retractable aperture 58 provides access for examination or surgical procedures while the membrane 16 isolates the lids 46, 48 and eyelashes 52, 54.

To remove the drape 10 at the end of the examination or surgical procedure, the filling tube 18 of at least the inner tubular member 12 is cut, allowing the member 12 to deflate. The flaccid inner tubular member 12 is then withdrawn from the cul-de-sac 50, and the drape 10 is discarded.

It should be noted that the drape 10 can dwell in a flat plane, or can assume the shape of a frusto-conical cone, depending on the radial width of the drape material between tubes 12 and 14. For example, for a planar shape, the fully inflated diameter of the inner and outer tubes 12 and 14 will be approximately 35 and 65 mm., respectively, and the distance therebetween would be approximately 15 mm. By increasing the distance to 25 mm., for example, the drape 10 would assume a frusto-conical shape. One skilled in the art can determine whether the planar or non-planar shape is best suited for a given procedure.

One skilled in the art will appreciate that the size, shape, and location of the surgical drape of this invention can be varied to suit the particular surgical need without detracting from the invention. This invention is also applicable to surgery on animals other than humans. For instance, eye surgery on various canine and feline breeds is not uncommon. The true essence and spirit of this invention are defined in the appended claims, and it is not intended that the embodiment of the invention presented herein should limit the scope thereof.

What is claimed is:

1. A barrier eye drape, comprising:
   an inner flexible tubular member having a first diameter adapted for insertion underneath the eyelids of a patient's eye and adapted to extend around the eyeball of a patient;
   an outer flexible tubular member having a second diameter greater than said first diameter and being adapted to engage the anterior surface of the eyelid of a patient,
   a flexible drape of sheet material extending between said inner and outer tubular members; and
   means for pumping fluid under pressure into said inner and outer flexible tubular members to inflate said members and draw said drape of sheet material into substantial planar contact with the interior and anterior portions of said eyelids.

2. The barrier eye drape of claim 1 wherein the inner tubular member forms a circular ring when inflated.

3. The barrier eye drape of claim 1 wherein the inner tubular member includes a plurality of striations thereon.

4. The barrier eye drape of claim 3 wherein said inner tubular member has an outer diameter and said striations extend circumferentially around said outer diameter.

5. The barrier eye drape of claim 1 wherein a liquid fluid is pumped into the tubular members by said means for pumping fluid.

6. The barrier eye drape of claim 1 wherein said means for pumping fluid is a syringe.

7. The barrier eye drape of claim 1 further comprising an elongated fluid filling tube having an end fluidly connected with said inner tubular member and another end having a self-sealing plug thereon for connection with said means for pumping fluid.

8. The barrier eye drape of claim 1 further comprising a second fluid filling tube having an end in fluid communication with said outer tubular member and another end having a self-sealing plug thereon for connection with said means for pumping fluid.

9. The barrier eye drape of claim 1 wherein said inner and outer tubular members and said flexible sheet are formed from a latex material.

10. A surgical drape for isolating an incision, comprising:

an inner flexible tubular membrane having a first diameter adapted for insertion into the body of a patient and circumscribing the interior of said incision, an outer flexible tubular membrane having a diameter greater than said first diameter and being adapted to engage the anterior surface of the patient's body around said incision, a flexible drape of sheet material extending between said inner and outer tubular members, and means for pumping fluid under pressure into said inner and outer flexible members to draw said drape into substantial planar contact with the interior and anterior portions of said incision.

11. The surgical drape of claim 10 wherein said inner and outer flexible tubular members are concentrically positioned with respect to each other.

12. A method for draping the eye of a patient during ophthalmic surgery, comprising:

providing a barrier eye drape with an inner flexible tubular member having a first diameter adapted for insertion underneath the eyelids of a patient's eye and adapted to extend around the eyeball of a patient, an outer flexible tubular member having a second diameter greater than said first diameter and being adapted to engage the anterior surface of the eyelid of a patient, a flexible sheet of drape material extending between said inner and outer tubular members, and means for pumping fluid under pressure into said inner and outer flexible members;

inserting said inner tubular member underneath the eyelids of the patient's eye so as to extend around the eyeball of the patient;

pumping fluid into said inner tubular member so as to inflate the inner tubular member into engagement with the eyelids of the patient' eye such that retaining pressure is created;

depositing the outer flexible tubular member on the outer surface of the eyelids;

pumping fluid into said outer flexible member so as to inflate said outer member to draw said drape material into substantially planar contact with the interior and anterior portions of said eyelids thereby retracting said eyelids outwardly and enlarging an opening there between;

whereby access to the eye for surgical procedures is provided and said inner tubular member provides a waterproof seal.

* * * * *